United States Patent [19]

Weetall

[11] 4,140,581

[45] Feb. 20, 1979

[54] IMMUNOASSAY OF NEISSERIA BACTERIA VIA $(NH_4)_2SO_4$ PRECIPITATION

[75] Inventor: Howard H. Weetall, Big Flats, N.Y.

[73] Assignee: Corning Glass Works, Corning, N.Y.

[21] Appl. No.: 837,363

[22] Filed: Sep. 28, 1977

[51] Int. Cl.$^2$ ............................................... C17K 1/04
[52] U.S. Cl. ........................... 195/103.5 A; 23/230 B; 195/103.5 M; 424/12
[58] Field of Search ................. 195/103.5 A, 103.5 R, 195/103.5 M; 424/12; 23/230 B

[56] References Cited

U.S. PATENT DOCUMENTS

| | | | |
|---|---|---|---|
| 3,773,625 | 11/1973 | Sternberger et al. | 195/103.5 A |
| 3,875,011 | 4/1975 | Rubenstein et al. | 195/103.5 A |
| 3,974,269 | 8/1976 | Maley | 195/103.5 A |
| 4,029,756 | 6/1977 | Gaafan | 195/103.5 A |

Primary Examiner—Thomas G. Wiseman
Attorney, Agent, or Firm—William E. Maycock; Clinton S. Janes, Jr.; Clarence R. Patty, Jr.

[57] ABSTRACT

This invention relates to means for determining the presence of Neisseria bacteria in a fluid sample, the method generally comprising reacting antibodies with an enzyme released during lysis of the fluid sample, and then testing for inhibition of activity of the enzyme. Inhibition of enzyme activity caused through the contact of antibodies specific to the enzyme can be readily detected. The enzyme released from Neisseria bacteria upon lysis possesses the faculty of oxidizing 1,2-propanediol and reducing nicotinamide-adenine-dinucleotide (NAD). Although the structure and behavior of the enzyme are not comprehended entirely, the above-mentioned faculty of the material has suggested the term 1,2-propanediol dehydrogenase therefor.

The specific inventive feature of the instant method is the use of $(NH_4)_2SO_4$ to precipitate the antigen-antibody complex which thereby concentrates the enzymes and can remove possibly interfering materials.

16 Claims, No Drawings

IMMUNOASSAY OF NEISSERIA BACTERIA VIA (NH$_4$)$_2$SO$_4$ PRECIPITATION

RELATED APPLICATIONS

U.S. Patent application Ser. No. 837,366, filed of even date by the present applicant entitled "Detecting Neisseria Bacteria", Patent application Ser. No. 837,365, filed of even date by the present applicant entitled "Comparative Test for Neisseria", U.S. Patent application Ser. No. 837,364, filed of even date by the present applicant entitled "Detection of Neisseria Bacteria by Immunoassay", U.S. Patent application Ser. No. 837,362, filed of even date by the present applicant entitled "Immunological Detection of Neisseria Bacteria Via Labelled Antibodies", Patent application Ser. No. 837,360, filed of even date by H. C. McDonald entitled "Detection and Quantitation of Neisseria Via Radioimmunoassay of an Enzyme Present in Neisseria Bacteria", and Patent application Ser. No. 837,361, filed of even date by M. M. Takeguchi and H. H. Weetall entitled "Transport System for Clinical Specimens", each of said applications being assigned to the assignee of the instant application.

BACKGROUND OF THE INVENTION

This disclosure relates generally to means for detecting the presence of Neisseria bacteria utilizing an immunoassay technique and is particularly directed to the use of (NH$_4$)$_2$SO$_4$ to precipitate the antigen-antibody complex.

The importance of being able to quickly and accurately detect the presence of Neisseria bacteria, especially *Neisseria gonorrhoeae*, is well recognized. Conventional tests for determining the presence of organisms such as *N. gonorrhoeae* require the preparation of bacteria cultures or the use of serological methods. Such tests, however, have known limitations. See, for example, the publication "International Symposium on Gonorrhea", B. B. Diena, Ed., a collection of papers presented at the Oct., 1973 International Symposium on Gonorrhea sponsored by the Health Protection Branch, Health and Welfare Canada, Ottawa, especially at p. 34 et seq.

In the related application cited above entitled "Detecting Neisseria Bacteria" there is disclosed a relatively simple and quick test for determining the presence of Neisseria in liquid samples. That test resulted from the discovery of an enzyme in Neisseria bacteria which appears to be specific to those organisms. The enzyme demonstrates the capability for oxidizing 1,2-propanediol and reducing nicotinamide-adenine-dinucleotide (NAD). Therefore, whereas the full compositional and structural parameters of the enzyme are not understood and no identification has been found in the literature, the oxidizing-reducing behavior exhibited by the enzyme has led to the application of the name 1,2-propanediol dehydrogenase thereto, and that application will be utilized throughout this specification.

It is well known that a specific biochemical reaction frequently takes place between an antibody and its homologous antigen thereby creating an antibody-antigen complex. Where an enzyme is the antigen, the reaction thereof with its specific antibody results in the activity of the enzyme being significantly inhibited. An excellent discussion of this phenomenon can be found in "Immunochemistry of Enzymes and Their Antibodies", M. J. Salton, John Wiley & Sons, New York (1977). Utilizing this reaction, then, one can detect the presence of a particular enzyme by bringing the antibody specific thereto into contact with the said enzyme and testing the result of the reaction therebetween for a decrease in enzyme activity.

The use of that practice for the determination of the presence of Neisseria bacteria in a liquid sample is described in the above-cited related application entitled "Detection of Neisseria Bacteria by Immunoassay". Hence, that invention is based upon using antibodies specific to the enzyme present in Neisseria bacteria, i.e., the 1,2-propanediol dehydrogenase described above, to inhibit the activity of the enzyme in an assay sample. In so doing, antibody specificity is inferred on the assay of the enzyme. Therefore, the procedure combines the sensitivity of an enzymatic reaction with the specificity of an immunoassay.

The instant invention comprises a modification of the method described in the latter patent application wherein (NH$_4$)$_2$SO$_4$ precipitation of the antigen-antibody complex acts to concentrate the enzyme, remove interfering materials, and, thereby, improve the speed and precision of the assay. The method is particularly useful with *N. gonorrhoeae*.

SUMMARY OF THE INVENTION

The method of the invention consists of the following nine general steps:
  (a) preparing a lysate of the fluid sample to be tested;
  (b) preparing an antiserum specific to 1,2-propanediol dehydrogenase;
  (c) combining the lysate and antiserum;
  (d) incubating the mixture of lysate and antiserum;
  (e) adding (NH$_4$)$_2$SO$_4$ to the mixture to cause precipitation;
  (f) removing the supernatant liquid;
  (g) adding buffer, NAD, and 1,2-propanediol to the precipitate;
  (h) incubating the mixture; and then
  (i) testing for activity of 1,2-propanediol dehydrogenase.

In a preferred embodiment of the invention, as demonstrated in the working examples reported hereinafter, the inhibition effect of the antiserum is explicitly exhibited through a comparative test wherein one sample is contacted with an antiserum and a second sample behaves as a control.

Thus, that method contemplates the following series of steps:
  (a) preparing a lysate of the fluid sample to be tested and dividing the lysate into two parts;
  (b) preparing an antiserum specific to 1,2-propanediol dehydrogenase;
  (c) contacting one part of the lysate with the antiserum;
  (d) contacting the second part of the lysate with non-specific globulin;
  (e) incubating the mixture of lysate and antiserum;
  (f) incubating the mixture of lysate and non-specific globulin;
  (g) adding (NH$_4$)$_2$SO$_4$ to each of the mixtures to cause precipitation;
  (h) removing the supernatant liquid from each mixture;
  (i) adding buffer, NAD, and 1,2-propanediol to each mixture;
  (j) incubating each mixture; and then (k) comparing the activity of 1,2-propanediol dehydrogenase in the two mixtures.

Incubation of the lysate with the antiserum causes a reaction to occur between the antibodies and the enzyme which results in inhibition of enzyme activity. This reduction in enzyme activity can be detected through such conventional techniques as fluorometry and spectrophotometry. Where a quantitative measure of the enzyme present is desired, such methods as radioimmunoassay, fluoroimmunoassay, and dipstick are available. In the following working examples, detection of enzyme inhibition was accomplished via fluorometry.

The addition of $(NH_4)_2SO_4$ to the lysate-antiserum mixture precipitates the enzyme-antibody complex, thereby concentrating the complex mixture and removing interfering materials. Such improves the sensitivity and specificity of the method.

Whereas the inventive method is operative with other species of Neisseria, the working examples reported below were directed to *N. gonorrhoeae*.

SPECIFIC EMBODIMENTS

In the first step, a sample, e.g., human body fluid or exudate, is contacted with a conventional cellular lysing agent to release intracellular contents, including enzymes. The lysing procedure need only be carried out under such conditions that denaturing of the enzyme of interest is avoided.

One method for preparing an operable lysate is described in the above-cited application entitled "Detecting Neisseria Bacteria" and that method is equally applicable here. Thus, a suspension of bacteria can be prepared in 0.03M TRIS buffer, PH 9.0. Egg-white lysozyme (Biozyme Laboratories) prepared in 0.03M TRIS buffer, pH 9.0, is admixed therewith and the mixture allowed to incubate, conveniently at room temperature (20°–25° C.). A chelating agent such as EDTA may optionally be included to bond with any divalent metal ions which might be present to interfere with the activity of these enzymes. The mixture is agitated and then centrifuged with the supernatant, which constitutes the lysate, being decanted off.

An antiserum is prepared in the known manner which can be used as such or in the form of a globulin fraction of the antibody. For ease in assay, a globulin fraction of the antibody will customarily be employed.

EXAMPLE I

A sample of bacterial lysate was prepared in the above manner having sufficient activity of 1,2-propanediol dehydrogenase to give an optical density change at 340 nm (viewed spectrophotometrically) of 0.08/minute in 0.1M TRIS, pH 9.0, containing 10 mg NAD and 3.5% by volume, 1,2-propanediol. This lysate was diluted with distilled water to 1:2000 and 1:4000 for assay purposes in a fluorometer. Other means for assaying the mixtures, e.g., utilizing spectrophotometry, are operable but fluorometry is particularly suitable here.

The diluted lysate was divided into two parts and to 0.1 ml of the first part was added 0.1 ml of antibody globulin diluted to 2 mg/ml. To 0.1 ml of the second part of the lysate was added 0.1 ml of non-specific globulin also diluted to 2 mg/ml. To each mixture was admixed 0.3 ml of 0.1M TRIS, pH 9.0, and the mixtures then permitted to incubate for 15 minutes at room temperature.

After incubation, 1.5 ml of a saturated aqueous solution of $(NH_4)_2SO_4$ were admixed to each mixture, each was allowed to stand 30 minutes, and thereafter each was centrifuged, the supernatant being decanted off and discarded. The addition of three volumes of $(NH_4)_2SO_4$ insures full precipitation of the antigen-antibody complex but greater or lesser amounts may be used as desired. Each precipitate was contacted with 3 ml of a solution consisting of 0.1M TRIS, pH 9.0, 100 mg/ml NAD, and 3.5% by volume, 1,2-propanediol. Each sample was then permitted to incubate for the times and temperatures stated below before being examined via a Turner Model III fluorometer utilizing a 7–60 primary filter and a 2A secondary filter. A comparison of the two samples was made by zeroing the instrument on the antibody sample and reading the non-specific; i.e., the antibody sample was utilized as the zero point. Consequently, if an enzyme (1,2-propanediol dehydrogenase) was present and inhibited, a change in fluorescence will be read on the other sample.

| Time | Dilution | Change in Fluoroescence | | | |
| --- | --- | --- | --- | --- | --- |
| | | 23° C. | 37° C. | 50° C. | 60° C. |
| 1 hr. | 1:2000 | 5.5 | 9 | 30 | 15 |
| | 1:4000 | 4.5 | 5.5 | 17 | 9 |
| 2 hrs. | 1:2000 | 10.5 | 17.5 | 55 | 19 |
| | 1:4000 | 7.5 | 9.5 | 37 | 12 |
| 3 hrs. | 1:2000 | 19 | 29.5 | | |
| | 1:4000 | 11.5 | 18 | | |
| 4 hrs. | 1:2000 | 21 | 32 | | |
| | 1:4000 | 14 | 20 | | |
| 5 hrs. | 1:2000 | 25.5 | 41.5 | | |
| | 1:4000 | 17.5 | 24 | | |
| 6 hrs. | 1:2000 | 33.5 | 46 | | |
| | 1:4000 | 19.5 | 29 | | |

From the above data it appears that better results are secured when the incubation is carried out at mildly elevated temperatures, viz., preferably up to about 50° C. but no more than about 60° C.

EXAMPLE II

A total of 143 cervical swabs were collected and shipped frozen in dry ice to Corning Glass Works, Corning, N.Y., for assay. The storage times, temperatures, etc. before receipt were unknown. The swabs were assayed using the present inventive method and employing the standard preparation of bacteria cultures.

Utilizing the present inventive method, 14 of the swabs gave a positive test for *N. gonorrhoeae*, whereas 15 positive cultures were observed, thereby indicating a correspondence of greater than 90% between the tests.

Thus, the present invention provides a relatively simple, quick, and accurate method for detecting the presence of Neisseria, and particularly *N. gonorrhoeae*, the method combining the sensitivity of an enzymatic reaction with the specificity of an immunoassay.

The operable pH values for lysis and incubation appear to range between about 7–10 with the preferred being about 8–9. Although incubation can occur at temperatures approaching 0° C., the rate of reaction between the antibodies and the enzyme contained within the lysate is greatly increased as the temperature of the antiserum-lysate is raised. The rate of reaction appears to reach an optimum at about 50° C. but decreases precipitously thereafter. Consequently, an incubation temperature of no greater than about 60° C. is deemed a practical maximum. However, the reaction rate at room temperature (20°–25° C.) is sufficiently rapid to justify the convenience of operating thereat.

It will be recognized that numerous modifications can be made to the method disclosed hereinabove. Therefore, the exemplary embodiments described in detail must be deemed to be illustrative only and not limitative. In sum, the scope of the invention is defined in the appended claims.

I claim:

1. In a method for detecting the presence of Neisseria bacteria in a fluid sample consisting of bringing antibodies specific to 1,2-propanediol dehydrogenase released from said bacteria during lysis thereof into contact with a lysed sample and reacting said antibodies with said enzyme forming a 1,2-propanediol dehydrogenase-antibody complex and then testing for inhibition of 1,2-propanediol dehydrogenase activity, the improvement comprising adding $(NH_4)_2SO_4$ to the mixture of lysate and antiserum to cause precipitation of the 1,2-propanediol dehydrogenase antibody complex.

2. A method according to claim 1 wherein said fluid sample is a human body fluid or exudate.

3. A method according to claim 1 wherein said Neisseria bacteria are of the species *N. gonorrhoeae*.

4. A method for detecting Neisseria bacteria in a fluid sample, the method consisting of the steps:
 (a) preparing a lysate of said sample;
 (b) preparing an antiserum specific to 1,2-propanediol dehydrogenase;
 (c) combining said lysate and antiserum;
 (d) incubating the resulting mixture of lysate and antiserum;
 (e) adding $(NH_4)_2SO_4$ to said resulting mixture to cause precipitation;
 (f) removing the resulting supernatant liquid; and then
 (g) assaying the mixture for activity of 1,2-propanediol dehydrogenase.

5. A method according to claim 4 wherein said fluid sample is a human body fluid or exudate.

6. A method according to claim 4 wherein $(NH_4)_2SO_4$ is added in an amount approximately three times per volume of that of the lysate-antiserum mixture.

7. A method according to claim 4 wherein said assay is carried out by:
 (a) adding buffer, nicotinamide adenine dinucleotide, and 1,2-propanediol to the precipitate;
 (b) incubating the resulting mixture; and then
 (c) testing for the activity of 1,2-propanediol dehydrogenase fluorometrically.

8. A method according to claim 7 wherein said incubations are carried out at a pH between about 7-10.

9. A method according to claim 7 wherein said lysis incubations are conducted at temperatures between about 0°-60° C.

10. A method according to claim 4 wherein said Neisseria bacteria are of the species *N. gonorrhoeae*.

11. A method for detecting Neisseria bacteria in a fluid sample, the method consisting of the steps:
 (a) preparing a lysate of the sample to be tested and dividing the lysate into two parts;
 (b) preparing an antiserum specific to 1,2-propanediol dehydrogenase;
 (c) contacting one part of the lysate with the antiserum;
 (d) contacting the second part of the lysate with non-specific globulin;
 (e) incubating the resulting mixture of lysate and antiserum;
 (f) incubating the resulting mixture of lysate and non-specific globulin;
 (g) adding $(NH_4)_2SO_4$ to each of the mixtures to cause precipitation therein;
 (h) removing the resulting supernatant liquid from each mixture;
 (i) adding buffer nicotinamide adenine dinucleotide, and 1,2-propanediol to each mixture;
 (j) incubating each mixture; and then
 (k) comparing the activity of 1,2-propanediol dehydrogenase in the two mixtures.

12. A method according to claim 11 wherein said fluid sample is a human body fluid or exudate.

13. A method according to claim 11 wherein $(NH_4)_2SO_4$ is added in an amount approximately three times per volume of that of the lysate-antiserum mixture or the lysate-non-specific globulin mixture.

14. A method according to claim 11 wherein said incubations are carried out at a pH between about 7-10.

15. A method according to claim 11 wherein said incubations are conducted at temperatures between about 0°-60° C.

16. A method according to claim 11 wherein said Neisseria bacteria are of the species *N. gonorrhoeae*.

* * * * *